(12) United States Patent
Manon-Jensen et al.

(10) Patent No.: US 12,391,747 B2
(45) Date of Patent: Aug. 19, 2025

(54) TYPE XXIII COLLAGEN ASSAY (71) Applicant: Nordic Bioscience A/S, Herlev (DK)

(72) Inventors: Tina Manon-Jensen, Brøndby (DK); Shu Sun, Farum (DK); Joachim Høg Mortensen, Hundige Strand (DK); Morten Karsdal, København Ø (DK)

(73) Assignee: Nordic Bioscience A/S, Herlev (DK)

( * ) Notice: Subject to any disclaimer, the term of this patent is extended or adjusted under 35 U.S.C. 154(b) by 1046 days.

(21) Appl. No.: 17/429,046

(22) PCT Filed: Feb. 6, 2020

(86) PCT No.: PCT/EP2020/053000
§ 371 (c)(1),
(2) Date: Aug. 6, 2021

(87) PCT Pub. No.: WO2020/161242
PCT Pub. Date: Aug. 13, 2020

(65) Prior Publication Data
US 2022/0227848 A1    Jul. 21, 2022

(30) Foreign Application Priority Data
Feb. 7, 2019  (GB) .................................... 1901710

(51) Int. Cl.
*C07K 16/18* (2006.01)
*G01N 33/68* (2006.01)

(52) U.S. Cl.
CPC .......... *C07K 16/18* (2013.01); *G01N 33/6887* (2013.01); *C07K 2317/33* (2013.01); *C07K 2317/34* (2013.01); *G01N 2333/78* (2013.01); *G01N 2800/065* (2013.01)

(58) Field of Classification Search
CPC ................ C07K 16/18; C07K 2317/33; C07K 2317/34; G01N 33/6887; G01N 2333/78; G01N 2800/065
See application file for complete search history.

(56) References Cited

PUBLICATIONS

Goel et al. The Journal of Immunology 173(12):7358-7367 (Year: 2004).*
Lloyd et al., Protein Engineering, Design & Selection 22(3):159-168 (Year: 2009).*
Edwards et al., Journal of Molecular Biology 334:103-118 (Year: 2003).*

* cited by examiner

*Primary Examiner* — Kimberly Ballard
*Assistant Examiner* — Stacey N MacFarlane
(74) *Attorney, Agent, or Firm* — Benjamin Aaron Adler (57) ABSTRACT The present invention provides monoclonal antibodies that target collagen type XXIII, and to immunoassays and kits employing the antibodies for detecting and quantifying the epitope. The invention also provides a method for identifying and monitoring subjects with inflammatory bowel disease.

10 Claims, 5 Drawing Sheets
Specification includes a Sequence Listing.

GLPVPGCWKH Type XXIII collagen (SEQ ID NO: 1)
GLPVQGCWNK Type XIII collagen (SEQ ID NO: 4)
GLPMPGCWQK Type XXV collagen (SEQ ID NO: 5)

Figure 1A

- selection, GLPVPGCWHK (SEQ ID NO: 1)
- elongated, GLPVPGCWHKA (SEQ ID NO: 16)
- truncated, GLPVPGCWH (SEQ ID NO: 3)
- deselection-1, GLPVQGCWNK, COL13 (SEQ ID NO: 4)
- deselection-2, GLPMPGCWQK, COL25 (SEQ ID NO: 5)

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial sequence
<220> FEATURE:
<223> OTHER INFORMATION: selection peptide sequence from C-terminus type
      XXIII collagen ?1 chain

<400> SEQUENCE: 1

Gly Leu Pro Val Pro Gly Cys Trp His Lys
1               5                   10

<210> SEQ ID NO 2
<211> LENGTH: 11
<212> TYPE: PRT
<213> ORGANISM: Artificial sequence
<220> FEATURE:
<223> OTHER INFORMATION: Elongated sequences of SEQ ID NO: 1
<220> FEATURE:
<221> NAME/KEY: SITE
<222> LOCATION: 11
<223> OTHER INFORMATION: Xaa is any amino acid

<400> SEQUENCE: 2

Gly Leu Pro Val Pro Gly Cys Trp His Lys Xaa
1               5                   10

<210> SEQ ID NO 3
<211> LENGTH: 9
<212> TYPE: PRT
<213> ORGANISM: Artificial sequence
<220> FEATURE:
<223> OTHER INFORMATION: Truncated sequence of SEQ ID NO: 1

<400> SEQUENCE: 3

Gly Leu Pro Val Pro Gly Cys Trp His
1               5
```

-continued

<210> SEQ ID NO 4
<211> LENGTH: 10
<212> TYPE: PRT
<213> ORGANISM: Artificial sequence
<220> FEATURE:
<223> OTHER INFORMATION: Sequence of deselection peptide from type XIII
      collagen

<400> SEQUENCE: 4

Gly Leu Pro Val Gln Gly Cys Trp Asn Lys
1               5                   10

<210> SEQ ID NO 5
<211> LENGTH: 10
<212> TYPE: PRT
<213> ORGANISM: Artificial sequence
<220> FEATURE:
<223> OTHER INFORMATION: Sequence of deselection peptide from type XXV
      collagen

<400> SEQUENCE: 5

Gly Leu Pro Met Pro Gly Cys Trp Gln Lys
1               5                   10

<210> SEQ ID NO 6
<211> LENGTH: 5
<212> TYPE: PRT
<213> ORGANISM: Artificial sequence
<220> FEATURE:
<223> OTHER INFORMATION: Sequence of monoclonal antibody
      complementarity-determining region CDR-H1

<400> SEQUENCE: 6

Ser Tyr Ala Met Ser
1               5

<210> SEQ ID NO 7
<211> LENGTH: 15
<212> TYPE: PRT
<213> ORGANISM: Artificial sequence
<220> FEATURE:
<223> OTHER INFORMATION: Sequence of monoclonal antibody
      complementarity-determining region CDR-H2

<400> SEQUENCE: 7

Ser Ile Ser Thr Ala Gly Arg Thr Tyr Tyr Pro Asp Thr Val Arg
1               5                   10                  15

<210> SEQ ID NO 8
<211> LENGTH: 10
<212> TYPE: PRT
<213> ORGANISM: Artificial sequence
<220> FEATURE:
<223> OTHER INFORMATION: Sequence of monoclonal antibody
      complementarity-determining region CDR-H3

<400> SEQUENCE: 8

Pro Asp Tyr Asp Tyr Asp Gly Tyr Ile Asn
1               5                   10

<210> SEQ ID NO 9
<211> LENGTH: 16
<212> TYPE: PRT
<213> ORGANISM: Artificial sequence
<220> FEATURE:
<223> OTHER INFORMATION: Sequence of monoclonal antibody
      complementarity-determining region CDR-L1

```
<400> SEQUENCE: 9

Arg Ser Ser Lys Ser Leu Leu His Ser Asn Gly Val Thr Tyr Leu Tyr
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: Sequence of monoclonal antibody
      complementarity-determining region CDR-L2

<400> SEQUENCE: 10

Gln Met Ser Asn Leu Ala Ser
1               5

<210> SEQ ID NO 11
<211> LENGTH: 9
<212> TYPE: PRT
<213> ORGANISM: Artificial sequence
<220> FEATURE:
<223> OTHER INFORMATION: Sequence of monoclonal antibody
      complementarity-determining region CDR-L3

<400> SEQUENCE: 11

Ala Gln Asn Leu Glu Leu Pro Leu Thr
1               5

<210> SEQ ID NO 12
<211> LENGTH: 89
<212> TYPE: PRT
<213> ORGANISM: Artificial sequence
<220> FEATURE:
<223> OTHER INFORMATION: Sequence of monoclonal antibody light chain CDR
      and framework region

<400> SEQUENCE: 12

Arg Ser Ser Lys Ser Leu Leu His Ser Asn Gly Val Thr Tyr Leu Tyr
1               5                   10                  15

Trp Tyr Leu Gln Lys Pro Gly Gln Ser Pro Gln Leu Leu Ile Tyr Gln
            20                  25                  30

Met Ser Asn Leu Ala Ser Gly Val Pro Asp Arg Phe Ser Ser Ser Gly
        35                  40                  45

Ser Gly Thr Asp Phe Thr Leu Arg Ile Ser Arg Val Glu Ala Glu Asp
    50                  55                  60

Val Gly Val Tyr Tyr Cys Ala Gln Asn Leu Glu Leu Pro Leu Thr Phe
65                  70                  75                  80

Gly Ala Gly Thr Lys Leu Glu Leu Lys
                85

<210> SEQ ID NO 13
<211> LENGTH: 88
<212> TYPE: PRT
<213> ORGANISM: Artificial sequence
<220> FEATURE:
<223> OTHER INFORMATION: Sequence of monoclonal antibody heavy chain CDR
      and framework region

<400> SEQUENCE: 13

Ser Tyr Ala Met Ser Trp Val Arg Gln Thr Pro Glu Lys Arg Leu Ala
1               5                   10                  15

Trp Val Ala Ser Ile Ser Thr Ala Gly Arg Thr Tyr Tyr Pro Asp Thr
            20                  25                  30
```

```
Val Arg Gly Arg Ile Thr Ile Ser Arg Asp Asn Ala Arg Asn Ile Leu
            35                   40                  45

Tyr Leu Gln Met Ser Ser Leu Arg Ser Glu Asp Thr Ala Ile Tyr Tyr
 50                      55                  60

Cys Ala Arg Pro Asp Tyr Asp Tyr Asp Gly Tyr Ile Asn Trp Gly Gln
 65                  70                  75                  80

Gly Thr Leu Val Thr Val Ser Ala
                85
```

<210> SEQ ID NO 14
<211> LENGTH: 112
<212> TYPE: PRT
<213> ORGANISM: Artificial sequence
<220> FEATURE:
<223> OTHER INFORMATION: Sequence of monoclonal antibody light chain variable region

<400> SEQUENCE: 14

```
Asp Ile Val Met Thr Gln Ala Ala Phe Ser Asn Pro Val Thr Leu Gly
 1               5                   10                  15

Thr Ser Ala Tyr Ile Ser Cys Arg Ser Ser Lys Ser Leu Leu His Ser
            20                  25                  30

Asn Gly Val Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
 50                      55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110
```

<210> SEQ ID NO 15
<211> LENGTH: 117
<212> TYPE: PRT
<213> ORGANISM: Artificial sequence
<220> FEATURE:
<223> OTHER INFORMATION: Sequence of monoclonal antibody heavy chain variable region

<400> SEQUENCE: 15

```
Val Lys Leu Val Glu Ser Gly Gly Gly Leu Val Lys Pro Gly Gly Ser
 1               5                   10                  15

Leu Lys Leu Ser Cys Ala Ala Ser Gly Phe Thr Phe Ser Ser Tyr Ala
            20                  25                  30

Met Ser Trp Val Arg Gln Thr Pro Glu Lys Arg Leu Ala Trp Val Ala
            35                  40                  45

Ser Ile Ser Thr Ala Gly Arg Thr Tyr Tyr Pro Asp Thr Val Arg Gly
 50                      55                  60

Arg Ile Thr Ile Ser Arg Asp Asn Ala Arg Asn Ile Leu Tyr Leu Gln
 65                  70                  75                  80

Met Ser Ser Leu Arg Ser Glu Asp Thr Ala Ile Tyr Tyr Cys Ala Arg
                85                  90                  95

Pro Asp Tyr Asp Tyr Asp Gly Tyr Ile Asn Trp Gly Gln Gly Thr Leu
            100                 105                 110

Val Thr Val Ser Ala
            115
```

<210> SEQ ID NO 16
<211> LENGTH: 11
<212> TYPE: PRT
<213> ORGANISM: Artificial sequence
<220> FEATURE:
<223> OTHER INFORMATION: Elongated peptide sequence

<400> SEQUENCE: 16

```
Gly Leu Pro Val Pro Gly Cys Trp His Lys Ala
1               5                   10
```

<210> SEQ ID NO 17
<211> LENGTH: 454
<212> TYPE: PRT
<213> ORGANISM: Artificial sequence
<220> FEATURE:
<223> OTHER INFORMATION: Sequence of monoclonal antibody heavy chain

<400> SEQUENCE: 17

```
Glu Val Lys Leu Val Glu Ser Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Ala Trp Val
        35                  40                  45

Ala Ser Ile Ser Thr Ala Gly Arg Thr Tyr Tyr Pro Asp Thr Val Arg
    50                  55                  60

Gly Arg Ile Thr Ile Ser Arg Asp Asn Ala Arg Asn Ile Leu Tyr Leu
65                  70                  75                  80

Gln Met Ser Ser Leu Arg Ser Glu Asp Thr Ala Ile Tyr Tyr Cys Ala
                85                  90                  95

Arg Pro Asp Tyr Asp Tyr Asp Gly Tyr Ile Asn Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300
```

```
Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
            325                 330                 335

Ser Pro Ile Glu Arg Thr Ile Ser Lys Ile Lys Gly Leu Val Arg Ala
        340                 345                 350

Pro Gln Val Tyr Ile Leu Pro Pro Ala Glu Gln Leu Ser Arg Lys
            355                 360                 365

Asp Val Ser Leu Thr Cys Leu Val Val Gly Phe Asn Pro Gly Asp Ile
    370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
            435                 440                 445

Ser Arg Ser Pro Gly Lys
    450

<210> SEQ ID NO 18
<211> LENGTH: 219
<212> TYPE: PRT
<213> ORGANISM: Artificial sequence
<220> FEATURE:
<223> OTHER INFORMATION: Sequence of monoclonal antibody light chain

<400> SEQUENCE: 18

Asp Ile Val Met Thr Gln Ala Ala Phe Ser Asn Pro Val Thr Leu Gly
1               5                   10                  15

Thr Ser Ala Tyr Ile Ser Cys Arg Ser Ser Lys Ser Leu Leu His Ser
            20                  25                  30

Asn Gly Val Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205
```

```
Pro Ile Val Lys Ser Phe Asn Arg Asn Glu Cys
    210                 215
```

TYPE XXIII COLLAGEN ASSAY

FIELD OF THE INVENTION

The present invention relates to monoclonal antibodies that target collagen type XXIII, and to immunoassays and kits employing said antibodies.

INTRODUCTION

Crohn's disease (CD) and ulcerative colitis (UC) are the two main gastrointestinal disorders of inflammatory bowel disease (IBD) with similar symptoms, such as heightened inflammatory response and structural damage of the intestine. CD can affect the entire gastrointestinal tract, while UC is primarily limited in the colonic mucosa [1]. The cause of IBD is not fully understood, but it is believed to have a genetic basis and an abnormal response of the immune system to environmental factors [2].

The epithelium of healthy gut is covered by a single layer of intestinal epithelial cells which form the protective barrier against bacteria and other foreign substances including antigens and toxins, and only have selective permeability of dietary nutrients [3,4]. The epithelium is important to maintain the health of the gut. However, in both CD and UC, the intestinal permeability is impaired which results in invasion of numerous of bacteria from the lumen into the intestinal tissue and increased influx of immune cells from the blood stream into the tissue [5,6] which leads to chronic inflammation of the gastrointestinal tract in IBD patients [7]. The tight link between the intestinal epithelial cells is regulated mainly by junctional complexes, which is composed of tight junctions, adherence junctions, and desmosomes [6]. Many studies have shown that some of the junction proteins were significantly down-regulated in IBD inflamed intestine tissue [8-11], which could be the main reason for intestine permeability loss in IBD.

Type XXIII collagen, a member of type II transmembrane protein, was firstly discovered in 2003 by Jacqueline Banyard et al in rat metastatic tumor cells [12]. In human non-small lung cancer cell line and clear cell renal cell carcinoma cell line, type XXIII collagen was found to be related to cell adhesion and metastasis [13,14]. Type XXIII collagen knockout in such cell lines resulted in altered expression of cell adhesion molecules and impaired cell adhesion [13,14], which indicated type XXIII collagen might be a regulator of cell adhesion. Type XXIII collagen is not only expressed in cancer cells. In embryonic mouse intestinal section staining, it was found to be expressed by the epithelial surface of intestines, suggesting it may have important role for cell-cell interactions [15].

Type XXIII collagen consists of a short cytoplasmic domain, a membrane-spanning domain, and a long ectodomain [12]. The ectodomain has several collagenous domains and interrupted by short non-collagenous domains [12]. The newly synthesized type XXIII collagen can be transported to cell surface as a transmembrane protein or cleaved intracellularly by furin and the ectodomain released to the extracellular matrix (ECM) [16]. However, the function of the cleavage is not yet understood. Studies have shown that type XXIII was up-regulated in a series of cancers [17-19] and could be used as potential biomarker in prostate cancer [18], non-small cell lung cancer [17] and clear cell renal cell carcinoma [14]. However, the use of type XXIII collagen as a biomarker in other diseases has not yet been defined.

U.S. Pat. No. 7,993,863 B (Zetter et al) describes collagen like gene (CLG) products which are expressed in human prostate cancer and breast cancer cells lines but not in normal adult, placenta, lung, liver, skeletal muscle, kidney or pancreas tissues. A C-terminal non-collagenous region with the sequence LDQPCPVGPDGLPVPGCWHK (denoted SEQ ID No.14) is also described. The authors note that this sequence has a high identity with transmembrane collagens XMII and XXV, and so concluded that it is potentially a bad epitope.

There is evidence that shows that active IBD patients have increased intestinal permeability compared to the inactive disease [20]. The junction/adhesion proteins, such as E-cadherin, β-catenin, are dramatically down-regulated in active inflamed tissue of IBD patients [8]. Therefore, methods for assessment of the intestinal permeability can be used to evaluate the disease burden [5]. However, there are only a few non-invasive biomarkers available. Fecal calprotectin, a protein which is mainly expressed by neutrophils, is the most promising biomarker in IBD. It correlates with endoscopic disease activity [21], can predict relapse [22] and monitor the response to the treatment [23]. But fecal calprotectin only measures inflammation in intestines, and not tissue-damage directly, as calprotectin is a small calcium-binding protein found mostly in neutrophilic granulocytes. Claudin-3, a tight junction protein, can be measured in urine and potentially reflect the tight junction loss [24]. There is only limited information on this biomarker, and it needs further investigation in human. Therefore, there is still huge need for non-invasive biomarkers for intestinal permeability assessment in IBD.

SUMMARY OF THE INVENTION

Since type XXIII collagen is expressed in the epithelial layer of intestine, it may be cleaved from the cell surface during epithelial damage in IBD. Moreover, as type XXIII collagen plays an important role in cell adhesion, the levels may be modulated and contribute to cell adhesive change in IBD and so can be used as a biomarker.

The present inventors have developed a monoclonal antibody that specifically recognises the ectodomain of Type XXIII collagen, specifically the C terminus of the al chain; and an immunoassay, in particular an enzyme-linked immunosorbent assay (ELISA) to detect the ectodomain of type XXIII collagen in a biofluid sample. The inventors have determined that Type XXIII collagen can be used as a biomarker of changes in cell adhesion and provide novel diagnostic information in patients with inflammatory bowel disease such as Crohn's disease (CD) and ulcerative colitis (UC).

Accordingly, in a first aspect the present invention relates to a monoclonal antibody that specifically recognises and binds to the C-terminus of type XXIII collagen al chain (also referred to herein as the target peptide), the C-terminus having the amino acid sequence GLPVPGCWHK (SEQ. ID No. 1) (also referred to herein as the target sequence).

Preferably, the monoclonal antibody is a monoclonal antibody that has been raised against a synthetic peptide having the C-terminus amino acid sequence GLPVPGCWHK (SEQ. ID No. 1). The synthetic peptide used to raise the antibody may be a synthetic peptide linked at its N-terminus to a carrier protein. Exemplary carrier proteins include proteins such as, but not limited to, keyhole limpet hemocyanin (KLH). The synthetic peptide may be linked to the carrier protein via any suitable linkage, which may include one or more additional amino acid residues at the N-terminus of the peptide. The monoclonal antibody may have been raised via suitable techniques known those skilled in the art such as, but not limited to, immunizing a mouse or other mammal, isolating and fusing spleen cells from the immunized mammal with hybridoma cells, and then culturing the resultant hybridoma cells to secure monoclonal growth.

In a preferred embodiment, the monoclonal antibody does not specifically recognise or bind to a peptide having the C-terminus amino acid sequence GLPVPGCWHKX (SEQ. ID No. 2), wherein X represents any amino acid. Thus, the monoclonal antibody preferably does not specifically recognise or bind to elongated variants of the target peptide in which the target amino acid sequence has been extended at the C-terminus by one or more amino acids.

In a preferred embodiment, the monoclonal antibody does not specifically recognise or bind to a peptide having the C-terminus amino acid sequence GLPVPGCWH (SEQ. ID No. 3). Thus, the monoclonal antibody preferably does not specifically recognise or bind to shortened variants of the target peptide in which the target amino acid sequence has been truncated at the C-terminus by one or more amino acids.

In a preferred embodiment, the monoclonal antibody does not specifically recognise or bind to a peptide having the C-terminus amino acid sequence GLPVQGCWNK (SEQ. ID No. 4). Thus, the monoclonal antibody preferably does not specifically recognise or bind to a peptide from type XIII collagen.

In a preferred embodiment, the monoclonal antibody does not specifically recognise or bind to a peptide having the C-terminus amino acid sequence GLPMPGCWQK (SEQ. ID No. 5). Thus, the monoclonal antibody preferably does not specifically recognise or bind to a peptide from type XXV collagen.

The monoclonal antibody or fragment thereof may preferably comprise one or more complementarity-determining regions (CDRs) selected from:

CDR-H1:
(SEQ. ID No. 6)
SYAMS

CDR-H2:
(SEQ. ID No. 7)
SISTAGRTYYPDTVR

CDR-H3:
(SEQ. ID No. 8)
PDYDYDGYIN

CDR-L1:
(SEQ. ID No. 9)
RSSKSLLHSNGVTYLY

CDR-L2:
(SEQ. ID No. 10)
QMSNLAS
and

CDR-L3:
(SEQ. ID No. 11)
AQNLELPLT

Preferably the antibody or fragment thereof comprises at least 2, 3, 4, 5 or 6 of the above listed CDR sequences.

Preferably the monoclonal antibody or fragment thereof has a light chain variable region comprising the CDR sequences CDR-L1:
(SEQ. ID No. 9)
RSSKSLLHSNGVTYLY CDR-L2:
(SEQ. ID No. 10)
QMSNLAS
and CDR-L3:
(SEQ. ID No. 11)
AQNLELPLT Preferably the monoclonal antibody or fragment thereof has a light chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

(SEQ ID No. 12)
RSSKSLLHSNGVTYLY_WYLQKPGQSPQLLIY_QMSNLAS_GVPDRFSSS_
_GSGTDFTLRISRVEAEDVGVYYC_AQNLELPLT_FGAGTKLELK_.

Preferably the monoclonal antibody or fragment thereof has a heavy chain variable region comprising the CDR sequences CDR-H1:
(SEQ. ID No. 6)
SYAMS CDR-H2:
(SEQ. ID No. 7)
SISTAGRTYYPDTVR CDR-H3:
(SEQ. ID No. 8)
PDYDYDGYIN.

Preferably the monoclonal antibody or fragment thereof has a heavy chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

(SEQ. ID No. 13)
SYAMS_WVRQTPEKRLAWVA_SISTAGRTYYPDTVRG_RITISRDNARNI_
_LYLQMSSLRSEDTAIYYCAR_PDYDYDGYIN_WGQGTLVTVSA_

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

(SEQ. ID No 14)
*DIVMTQAAFSNPVTLGTSAYISC*__RSSKSLLHSNGVTYLY__*WYLQKPGQ*

*SPQLLIY*__QMSNLAS__*GVPDRFSSSGSGTDFTLRISRVEAEDVGVYYC*__A__

__QNLELPLT__*FGAGTKLELK* and/or the heavy chain variable region sequence:

(SEQ. ID No. 15)
*VKLVESGGGLVKPGGSLKLSCAASGFTFSS*__SYAMS__*WVRQTPEKRLAWV*

*A*__SISTAGRTYYPDTVRG__*RITISRDNARNILYLQMSSLRSEDTAIYYC*

*ARP*__DYDYDGYIN__*WGQGTLVTVSA*

(CDRs bold and underlined; Framework sequences in italics)

In a second aspect, the present invention relates to a method of immunoassay for detecting type XXIII collagen in a human biofluid sample, said method comprising contacting a human biofluid sample with a monoclonal antibody according to the first aspect of the invention, and detecting binding between the monoclonal antibody and peptides in the sample.

Preferably, the detection is quantitative. Thus the method may comprise detecting and determining the amount of binding between the monoclonal antibody and peptides in the sample.

Preferably, the immunoassay is a competitive immunoassay.

Preferably, the immunoassay is an enzyme-linked immunosorbent assay (ELISA). Preferably the ELISA is a competitive ELISA.

The human biofluid sample may be for instance blood, serum, plasma or urine. Preferably the sample is serum or plasma.

The human biofluid sample may be a sample from a human patient having medical signs or symptoms indicative of inflammatory bowel disease. Preferably the biofluid sample is a sample from a human patient having medical signs or symptoms indicative of Crohn's disease (CD) or ulcerative colitis (UC). Preferably the biofluid sample is a sample from a human patient having medical signs or symptoms indicative of active inflammatory bowel disease, for example active Crohn's disease (CD) or active ulcerative colitis (UC).

The method may be an immunoassay method for diagnosing and/or monitoring and/or assessing the likelihood of inflammatory bowel disease in a patient, the method comprising contacting a biofluid sample obtained from said patient with the monoclonal antibody, detecting and determining the amount of binding between the monoclonal antibody and peptides in the sample, and correlating said amount of binding with values associated with normal healthy subjects and/or values associated with known disease severity and/or values obtained from said patient at a previous time point. Preferably the inflammatory bowel disease is Crohn's disease or ulcerative colitis. Preferably the inflammatory bowel disease is active inflammatory bowel disease, for example active Crohn's disease (CD) or active ulcerative colitis (UC).

In a third aspect, the present invention relates to an assay kit comprising a monoclonal antibody according to the first aspect of the invention, and at least one of:
- a streptavidin coated well plate;
- a N-terminal biotinylated peptide having the C-terminus amino acid sequence GLPVPGCWHK (SEQ. ID No. 1); and
- a calibrator peptide having the C-terminus amino acid sequence GLPVPGCWHK (SEQ. ID No. 1).

The kit may be for use in diagnosing or predicting the risk of inflammatory bowel disease, preferably in conjunction with the methods according to the second aspect of the invention. Preferably the inflammatory bowel disease is Crohn's disease or ulcerative colitis. The inflammatory bowel disease is preferably active inflammatory bowel disease e.g. active Crohn's disease or active ulcerative colitis.

Definitions

As used herein, the terms "peptide" and "polypeptide" are used synonymously.

As used herein the term "monoclonal antibody" refers to both whole antibodies and to fragments thereof that retain the binding specificity of the whole antibody, such as for example a Fab fragment, Fv fragment, or other such fragments known to those skilled in the art. Antibodies which retain the same binding specificity may contain the same complementarity-determining regions (CDR). The CDR of an antibody can be determined using methods know in the art such as that described by Kabat et al.[28]

Antibodies can be generated from B cell clones as described in the examples. The isotype of the antibody can be determined by ELISA specific for human IgM, IgG or IgA isotype, or human IgG1, IgG2, IgG3 or IgG4 subclasses. Other suitable methods can be used to identify the isotype.

The amino acid sequence of the antibodies generated can be determined using standard techniques. For example RNA can be isolated from the cells, and used to generate cDNA by reverse transcription. The cDNA is then subjected to PCR using primers which amplify the heavy and light chains of the antibody. For example primers specific for the leader sequence for all VH (variable heavy chain) sequences can be used together with primers that bind to a sequence located in the constant region of the isotype which has been previously determined. The light chain can be amplified using primers which bind to the 3' end of the Kappa or Lamda chain together with primers which anneal to the V kappa or V lambda leader sequence. The full length heavy and light chains can be generated and sequenced.

As used herein the term "C-terminus" refers to the extremity of a polypeptide, i.e. at the C-terminal end of the polypeptide, and is not to be construed as meaning in the general direction thereof. Likewise, the term "N-terminus" refers to the extremity of a polypeptide, i.e. at the N-terminal end of the polypeptide, and is not to be construed as meaning in the general direction thereof.

As used herein the term, the term "competitive immunoassay" refers to an immunoassay in which the target peptide present in a sample (if any) competes with known amount of target of peptide (which for example is bound to a fixed substrate or is labelled) for to binding an antibody, which is a technique known to those skilled in the art.

As used herein the term "ELISA" (enzyme-linked immunosorbent assay) refers to an immunoassay in which the target peptide present in a sample (if any) is detected using antibodies linked to an enzyme, such as horseradish peroxidase or alkaline phosphatase. The activity of the enzyme is then assessed by incubation with a substrate generating a measurable product. The presence and/or amount of target peptide in a sample can thereby be detected and/or quantified. ELISA is a technique known to those skilled in the art.

As used herein the term "amount of binding" refers to the quantification of binding between monoclonal antibody and target peptide, which said quantification is determined by comparing the measured values of target peptide in the biofluid samples against a calibration curve, wherein the calibration curve is produced using standard samples of known concentration of the target peptide. In the specific assay disclosed herein which measures in biofluids target peptides having the C-terminus amino acid sequence GLPVPGCWHK (SEQ. ID No. 1), the calibration curve is produced using standard samples of known concentration of a calibration peptide having the C-terminus amino acid sequence GLPVPGCWHK (SEQ. ID No. 1, (and which may in particular consist of the amino acid sequence GLPVPGCWHK (SEQ. ID No. 1)). The values measured in the biofluid samples are compared to the calibration curve to determine the actual quantity of target peptide in the sample.

As used herein, the term "PRO-C23" refers to type XXIII collagen ectodomain having the C-terminal amino acid sequence GLPVPGCWHK (SEQ. ID No. 1).

FIGURES

FIGS. 1A-1C: PRO-C23 antibody 10F6 specificity.

FIGS. 3A-3B: PRO-C23 levels in rat DSS model.

EXAMPLES

Various embodiments are described and disclosed in the following Examples, which are set forth to aid in the understanding of the present disclosure and should not be construed to limit in any way the scope of the invention as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods

Antibody Development for PRO-C23

The last 10 amino acids of the type XXIII collagen al chain ($^{531}$'GLPVPGCWHK'$^{540}$, (SEQ. ID No. 1) Genscript, USA) were used as the immunogenic peptide to generate specific monoclonal antibodies. 4-6-week-old Balb/C mice were immunized subcutaneously with 100 μg of the immunogen (KLH-CGG-GLPVPGCWHK (SEQ. ID No. 1) emulsified with Stimmune adjuvant (Thermo Fisher, USA). Consecutive immunizations were performed at 2-week intervals. The mouse with highest antiserum titer and the best peptide reactivity was selected for fusion. Mouse spleen cells were fused with SP2/0 myeloma cells. The fusion cells were raised in 96-well plates and incubated in the CO2-incubator. Cell lines specific to the selection peptide and without cross-reactivity to neither elongated peptide (GLPVPGCWHKA (SEQ. ID No. 16)), truncated peptide (GLPVPGCWH) nor deselection peptides (GLPVQGCWNK, (SEQ. ID. No. 4) type XIII collagen, GLPMPGCWQK (SEQ ID No. 5), type XXV collagen) (Genscript, USA) were selected and subcloned. At last, the antibodies were purified using an IgG column (GE health, USA).

The antibodies generated were sequenced and the CDRs determined.

The sequence of the chains are as follows:

CDRs underlined and in bold

Constant Region Italic:

Heavy chain: Amino acid sequence (454 aa)
(SEQ. ID No. 17)
EVKLVESGGGLVKPGGSLKLSCAASGFTFSSYAMSWVRQTPEKRLAW

VASISTAGRTYYPDTVRGRITISRDNARNILYLQMSSLRSEDTAIYY

CARPDYDYDGYINWGQGTLVTVSAAKTTPPSVYPLAPGCGDTTGSSV

TLGCLVKGYFPESVTVTWNSGSLSSSVHTFPALLQSGLYTMSSSVTV

PSSTWPSQTVTCSVAHPASSTTVDKKLEPSGPISTINPCPPCKECHK

CPAPNIEGGPSVFIFPPNIKDVLMISLTPKVTCVVVDVSEDDPDVQI

SWFVNNVEVHTAQTQTHREDYNSTIRVVSTLPIQHQDWMSGKEFKCK

VNNKDLPSPIERTISKIKGLVRAPQVYILPPPAEQLSRKDVSLTCLV

-continued

VGFNPGDISVEWTSNGHTEENYKDTAPVLDSDGSYFIYSKLNMKTSK

WEKTDSFSCNVRHEGLKNYYLKKTISRSPGK

Light chain: Amino acid sequence (219 aa)
(SEQ. ID No. 18)
DIVMTQAAFSNPVTLGTSAYISCRSSKSLLHSNGVTYLYWYLQKPGQ

SPQLLIYQMSNLASGVPDRFSSSGSGTDFTLRISRVEAEDVGVYYCA

QNLELPLTFGAGTKLELKRADAAPTVSIFPPSSEQLTSGGASVVCFL

NNFYPKDINVKWKIDGSERQNGVLNSWTDQDSKDSTYSMSSTLTLTK

DEYERHNSYTCEATHKTSTSPIVKSFNRNEC

PRO-C23 Assay and Technical Evaluation

ELISA-plates used for the assay development were Streptavidin-coated from Roche (cat.: 11940279). All ELISA plates were analyzed with the ELISA reader from Molecular Devices, SpectraMax M, (CA, USA). The selected monoclonal antibody was labelled with horseradish peroxidase (HRP) using the Lightning link HRP labeling kit according to the instructions of the manufacturer (Innovabioscience, Babraham, Cambridge, UK). A 96-well streptavidin plate was coated with biotin-GLPVPGCWHK (SEQ. ID No. 1) (Genscript, USA) and incubated 30 minutes at 20° C. 20 µL of standard peptide or samples were added to appropriate wells, followed by 100 µL of HRP conjugated monoclonal antibody 10F6, and incubated 20 hour at 4° C. Finally, 100 µL tetramethylbenzidine (TMB) (Kem-En-Tec cat.4380H) was added and the plate was incubated 15 minutes at ° C. in the dark. All the above incubation steps included shaking at 300 rpm. After each incubation step, the plate was washed five times. The TMB reaction was stopped by adding 100 µL of stopping solution (1% $H_2SO_4$) and measured at 450 nm with 650 nm as the reference.

The lower limit of detection (LLOD) was determined from 21 zero samples (i.e. buffer) and calculated as the mean+3× standard deviation. Upper limit of detection (ULOD) was determined as the mean−3×SD of 10 measurements of Standard A. The intra-assay and inter-assay variation was the mean variations of 10 QC samples run 10 independent times in duplicate. Dilution recovery was determined in 4 serum samples and 4 plasma samples and was calculated as a percentage of recovery of diluted samples from the 100% sample. Correlation between serum and plasma was determined in serum and the matched heparin plasma, citrate plasma, EDTA plasma from 16 individuals (Innovative Research, USA).

Western Blotting with Recombinant Human Type XXIII Collagen

Recombinant human type XXIII collagen (R&D system, 4165-CL) was diluted in sample buffer containing 80 mM DTT and run on a 10% SDS-PAGE gel, and subsequently transferred onto a nitrocellulose membrane. The nitrocellulose membranes were then blocked for non-specific binding by incubation for 1 hour at room temperature in TBS-T containing 5% skim milk powder. This was followed by incubation with 1 µg/ml 10F6 or commercial type XXIII collagen antibody (R&D system, MAB4165) diluted in TBS-T milk for overnight. Then the membranes were washed in TBS-T three times, followed by incubation in the secondary peroxidase conjugated antibody. Finally, the membranes were washed in TBS-T three times, and then the results were visualized using the ECL system (GE healthcare, cat #RPN2109).

DSS Rat Model

Male Sprague-Dawley rats, 12 weeks of age, were divided into 2 groups: 6% DSS group (12 rats) and a control group (9 rats). Acute colitis was induced in the DSS group by adding 6% of DSS to the drinking water for 5 days. After day 5, DSS was withdrawn from drinking water. Half of the rats in 6% DSS group and 3 control rats were sacrificed at day 6 to remove colon. The remaining the rats were allowed to recover from the DSS induced colitis until sacrifice at day 16. Blood samples were taken at baseline, day 6, 7 and 16. Disease activity index (DAI) was scored every day to evaluate the progression of colitis. It was based on the following parameters: weight loss, stool consistency and blood in feces or rectal bleeding. The weight loss score in DSS rats was compared to the mean weight of age-matched controls: score 0=0-4% weight loss; score 1=5-10.9% weight loss; score 2=11-15.9% weight loss; score 3=16-20% weight loss. Stool consistency: score 0=normal and well formed; score 1=soft and sticky stool visible at base of tail; score 2=very soft and unformed; score 4=diarrhoea and watery stool. Blood in feces or rectal bleeding: score 0=normal color stool; score 2=reddish color stool; score 4=bloody stool or bleeding from rectum. The score for each parameter resulted in a daily total DAI score ranging between 0 and 12. A total score of 5 or above was considered as high disease activity.

IBD Cohorts

Three different cohorts were measured to evaluate biological relevance of PRO-C23 assay. Serum samples were collected after informed consent and approval by the local Ethics Committee. In cohort 1, serum from CD and UC patients were obtained from commercial vendor Reprocell (USA), whereas as the serum from healthy donors were obtained from Valley Biomedical (USA) (table 1). In cohort 2 and cohort 3, serum from patients with CD and UC were obtained, respectively (table 2) For any of the cohorts, there were no significant statistical differences between the patient demographics (gender and age) of healthy donors, CD and UC patients.

TABLE 1

Patient demographics of cohort 1

|  | Healthy controls (N = 10) | CD (N = 10) | UC (N = 10) | P value |
|---|---|---|---|---|
| Age | 43.5 | 40.5 | 45.5 | 0.57 |
| Male, n (%) | 7 (70%) | 8 (80%) | 7 (70%) | 0.85 |

Comparison of age and gender was performed using Kruskal-Wallis test.
P-values below 0.05 were considered significant.
Abbreviations: CD: Crohn's disease, UC: Ulcerative colitis.

TABLE 2

Patient demographics of cohort 2 and 3

| General | Crohn's disease (cohort 2) | Ulcerative colitis (cohort 3) | Healthy donors | P-value |
|---|---|---|---|---|
| Total samples | 44 | 29 | 29 | 0.599 |
| Gender: n (%) female | 16 (37%) | 14 (41%) | 12 (41%) | |
| Age (years, mean [range]) | 36 [19-73] | 39 [17-62] | 38 [22-58] | 0.392 |
| Crohn's Disease Activity Index (CDAI) >150 | 24 (54%) | | NA | |

TABLE 2-continued

Patient demographics of cohort 2 and 3

| General | Crohn's disease (cohort 2) | Ulcerative colitis (cohort 3) | Healthy donors | P-value |
|---|---|---|---|---|
| Partiel mayo score (>1) | NA | 14 (48%) | | |
| Age at diagnosis (n(%)) | | | NA | |
| A1 (<16) | 0 (0%) | | | |
| A2 (17-40) | 31 (71%) | | | |
| A3 (>40) | 13 (29%) | | | |
| Disease location start IFx (n(%)) | | | NA | |
| L1 (n, %) | 5 (11%) | | | |
| L2 (n, %) | 14 (32%) | | | |
| L3 (n, %) | 25 (57%) | | | |
| Disease behavior start IFx (n(%)) | | | NA | |
| B1: Luminal disease | 20 (45%) | | | |
| B2: Stricturing | 11 (25%) | | | |
| B3: Penetrating | 13 (30%) | | | |
| Disease extension | | | NA | |
| E1: proctitis | | 2 (7%) | | |
| E2: Left-sided | | 8 (28%) | | |
| E3: Pan-colitis | | 19 (66%) | | |
| Disease severity | | | NA | |
| S1: Mild | | 15 (52%) | | |
| S2: Moderate | | 13 (45%) | | |
| S3: Severe | | 1 (3%) | | |
| Peri-anal disease | 0 | 0 | NA | |

Comparison of age and gender was performed using a Mann-Whitney U test or fisher's exact test.
P-values below 0.05 were considered significant.
Abbreviations: CD: Crohn's disease.

Statistics

Statistical analysis was performed using MedCalc version 14 and GraphPad Prism version 7. The biomarker levels were presented as median ±95% confidence interval. The differences of PRO-C23 between DSS rats and controls were determined by unpaired t-test. In human cohorts, comparison of age and gender was performed using a Kruskal-Wallis test. The differences of PRO-C23 between patients and healthy controls were determined by Mann-Whitney t-test. The diagnostic power of biomarkers was investigated by the area under the receiver-operating characteristics (ROC) curve (AUC) with 95% confidence interval (CI). Sensitivity and specificity were determined for appropriate cut-off values based on the ROC curves. Significance threshold was set at P<0.05.

Results

Characterization of PRO-C23 Assay

Figure 1A:
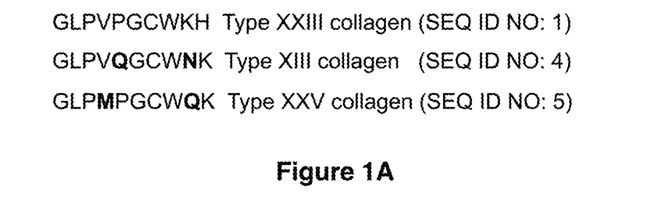
FIG. 1A) Sequence alignment for C-terminus of type XIII, XXIII and XXV collagens. The antibody recognizes the residues from 531 to 540 of type XXIII collagen.
Figure 1B:
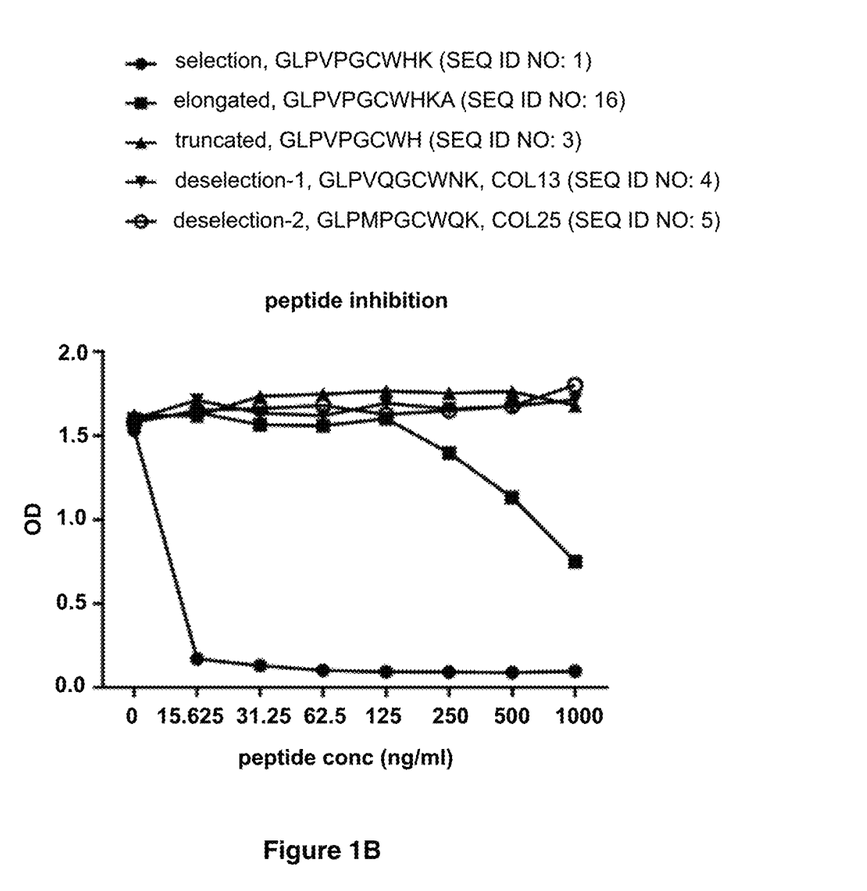
FIG. 1B) PRO-C23 antibody specificity towards different peptides. Reactivity to the selection peptide (GLPVPGCWHK (SEQ. ID No. 1)), the elongated peptide (GLPVPGCWHKA (SEQ. ID No. 16)), the truncated peptide (GLPVPGCWH), peptide from type XIII collagen (GLPVQGCWNK (SEQ. ID. No. 4)) and peptide from type XXV collagen (GLPMPGCWQK (SEQ. ID No. 5)) was tested in the PRO-C23 assay.
Figure 1C:
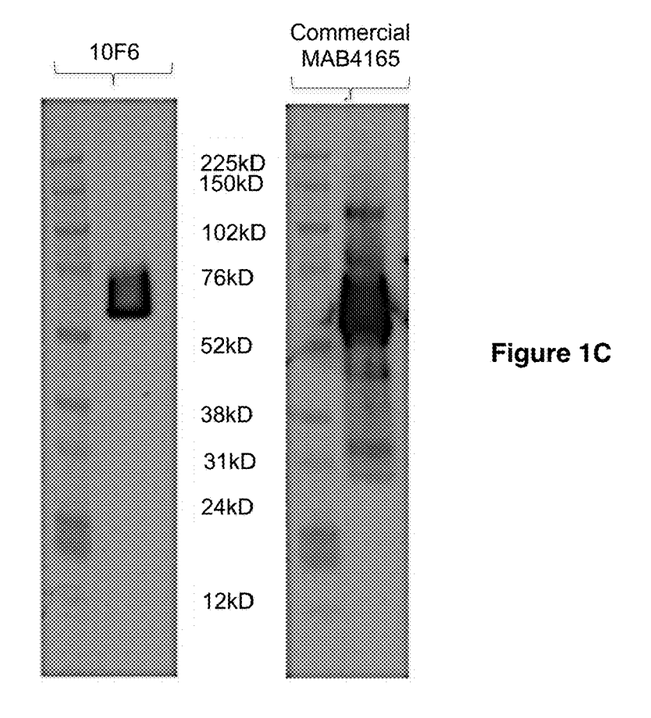
FIG. 1C) Western blot results of recombinant type XXIII collagen using 10F6 as primary antibody.

Like type XXIII collagen, type XIII and XXV collagens are also transmembrane collagens and share highly similar sequences in their C-terminus (FIG. 1A). To fully investigate the specificity of the antibody, a series of peptides were synthesized and included in the inhibition test. The chosen antibody 10F6 specifically recognized the last 10 amino acids of C-terminus of type XXIII collagen $^{531}$'GLPVPGCWHK'$^{540}$, (SEQ. ID No. 1) but did not recognize elongated peptide GLPVPGCWHKA (SEQ. ID No. 16), truncated peptide GLPVPGCWH(SEQ. ID No. 3), type XIII collagen C-terminal peptide GLPVQGCWNK (SEQ. ID. No. 4), or type XXV collagen C-terminal peptide GLPMPGCWQK. (SEQ. ID No. 5) (FIG. 1B). Western blot of recombinant type XXIII collagen ectodomain (4165-CL, R&D system) showed that the chosen antibody 10F6 recognized type XXIII collagen ectodomain around 60 kD, while reference commercial antibody (MAB4165, R&D system) was also shown (FIG. 1C).

Figure 2:
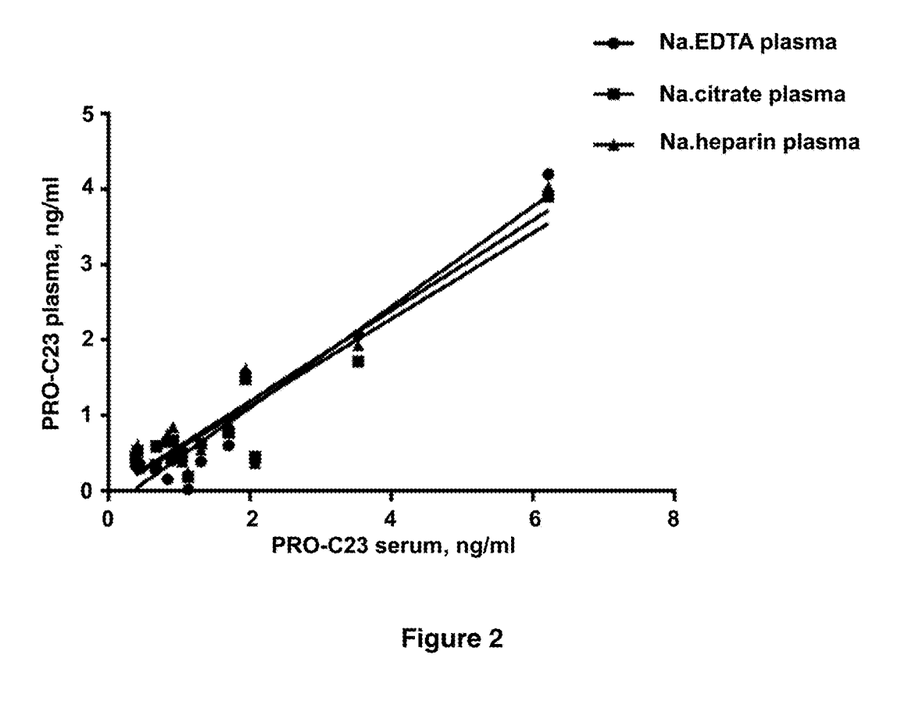
FIG. 2: Correlation of PRO-C23 levels in three kinds of plasma and serum (N=16)

PRO-C23 competitive ELISA provided a measurement range from 0.38 ng/ml (LLOD) to 18.73 ng/ml (ULOD). The inter- and intra-assay variability were 8.1% and 3.5%, respectively. The dilution recovery and spiking recovery in human serum was shown in Table 3. The correlations between values in human serum and three kinds of plasmas were relatively high (FIG. 2, P<0.0001), showing that PRO-C23 levels were independent of blood preparation method.

TABLE 3

Technical performance of PRO-C23 assay

| | |
|---|---|
| Detection range (LLOD-ULOD) | 0.38 ng/mL-18.73 ng/mL |
| Intra-assay variability | 3.5% |
| Inter-assay variability | 8.1% |
| Dilution recovery in serum | Within 100 ± 20% |
| Spiking recovery in serum | 75.8% |
| Interference | No HAMA, biotin, intralipid and hemoglobin interference |

PRO-C23 Biomarker in DSS Rat Model

Figure 3A:
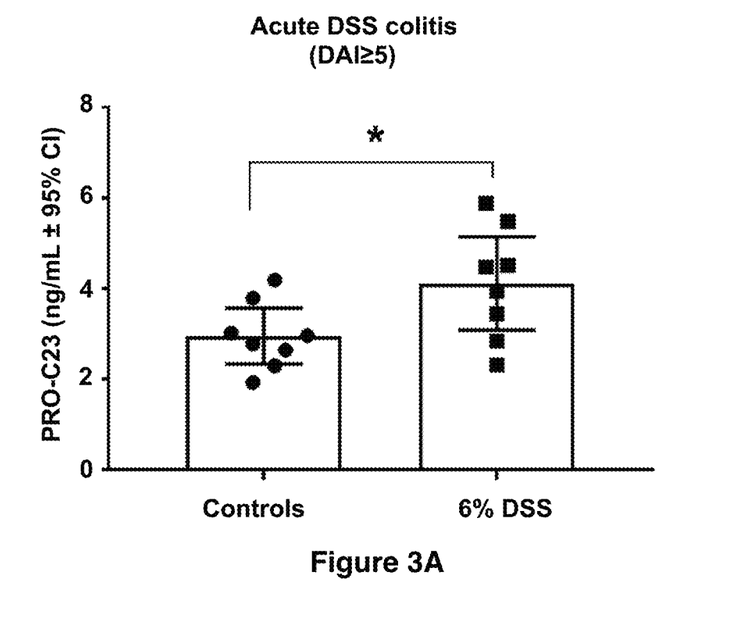
FIG. 3A) PRO-C23 serum levels in control rats (n=8) and DSS rats with DAI≥5 (n=8).
Figure 3B:
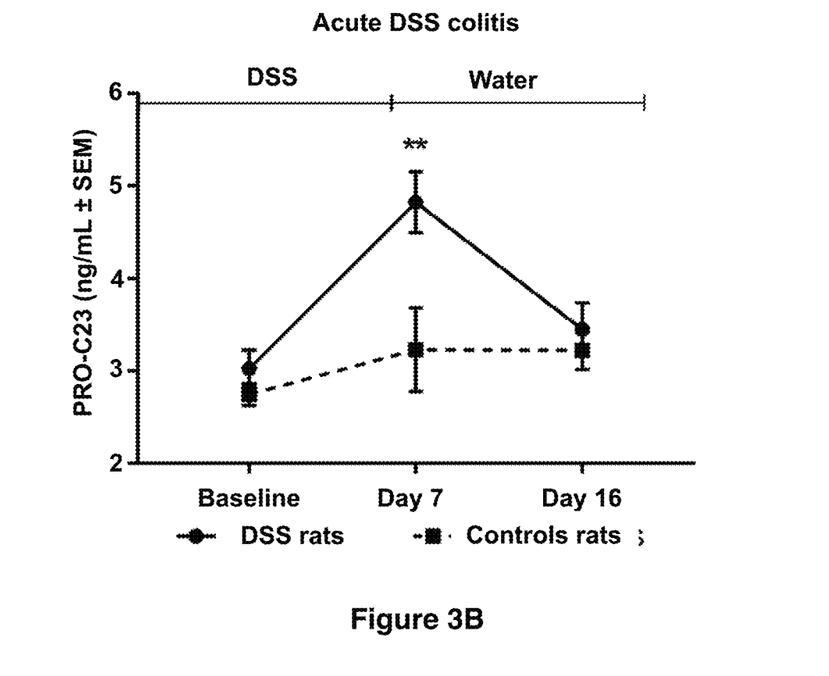
FIG. 3B) The serum levels of PRO-C23 increased upon induction of colitis and returned towards baseline at reversal of the intestinal inflammation. Data are presented as median+95% confidence interval. * Asterisk (*) represent statistical difference. P<0.05.

To investigate the biological relevance of PRO-C23 fragment, a rat model of DSS induced colitis was used. PRO-C23 biomarker was measured in serum samples. DSS rats with high disease activity index (DAI≥5) at day 6 and 7 had significantly higher PRO-C23 serum levels (p>0.05, FIG. 3A) compared to controls. The serum levels of PRO-C23 increased upon induction of colitis and returned towards baseline at reversal of the intestinal inflammation (FIG. 3B).

PRO-C23 Biomarker in Human IBD Cohorts

Figure 4:
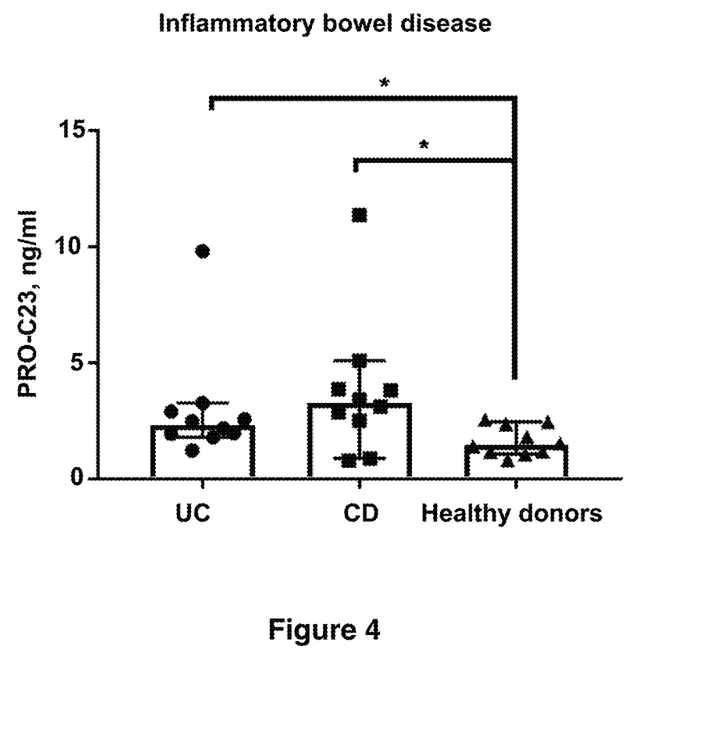
FIG. 4: PRO-C23 levels in human cohort 1. Data are presented as median ±95% confidence interval. * Asterisk (*) represent statistical difference. * P<0.05.
Figure 5A:
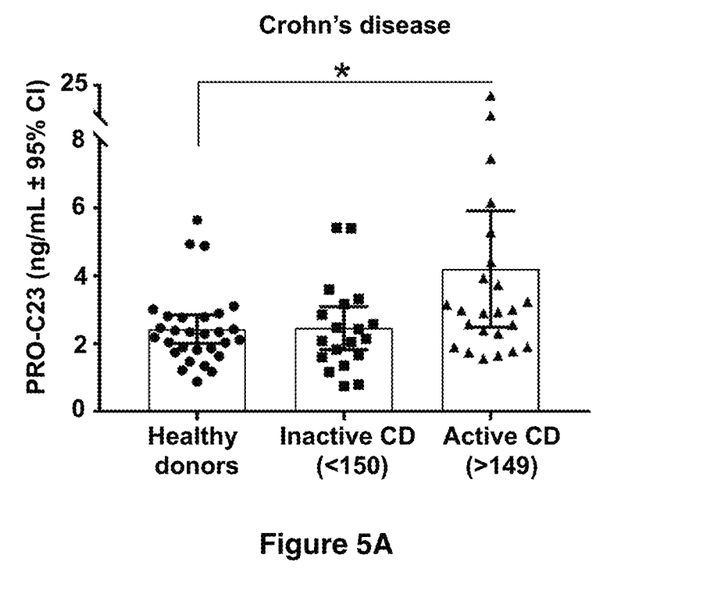
FIGS. 5A-5B: PRO-C23 levels in human cohort 2 (CD) and 3 (UC). Data are presented as median+95% confidence interval. * Asterisks (*) represent statistical differences. * (p<0.05)  (p<0.01) * (p<0.001)
Figure 5B:
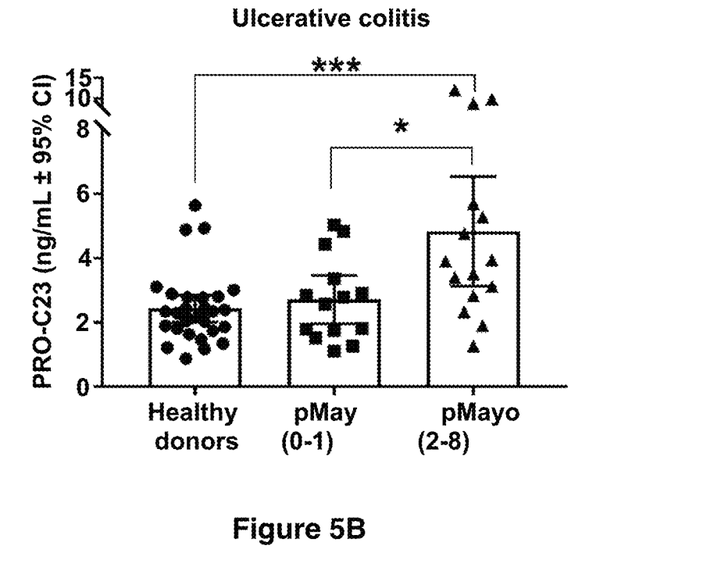

PRO-C23 was measured in serum from three independent human cohorts. In cohort 1, PRO-C23 were quantified in 10 CD and 10 UC patients, together with 10 age-matched healthy donors. Results showed that CD and UC patients have significantly higher levels of PRO-C23 (p<0.05, FIG. 4) compared to healthy donors. No information of the activity of the disease in these patients was given. In cohort 2 and 3, 44 CD patients and 29 UC patients were included, together with 29 age-matched healthy donors. PRO-C23 levels were elevated in active CD patients and active UC patients compared to healthy donors (CD: p<0.05, UC: p<0.001 FIGS. 5A-5B).

DISCUSSION

It was hypothesized that type XXIII collagen could be cleaved from cell surface during epithelial damage. Moreover, the loss of type XXIII collagen could contribute to the epithelial adhesion change in IBD and so used as a biomarker for IBD. Therefore, a PRO-C23 ELISA measuring the ectodomain of type XXIII collagen was developed.

The antibody only recognized the C-terminus sequence of type XXIII collagen and had no cross-reaction with C-terminus of type XIII and XXV collagen which showed similar sequences. This data clearly confirmed the specificity of the antibody. Thereafter, the antibody was applied in a competitive ELISA and optimized for human serum and plasma measurement. The data demonstrated that the ectodomain of type XXIII could be detected in circulation by the competitive ELISA independent of blood preparation method.

In order to further validate the biomarker in in vivo studies, the PRO-C23 biomarker was measured in a DSS induced colitis rat model. DSS can cause intestinal epithelial cell injury. The animals exhibit IBD-like symptoms, such as diarrhoea, rectal bleeding and weight loss [25,26]. One study also showed that DSS can induce altered tight junction protein expression [27]. Therefore, DSS rat model could be an appropriate animal model to validate PRO-C23 biomarker. Type XXIII collagen was found to be elevated in rats with active disease and weakly correlated with disease activity. This finding indicated the ectodomain of type XXIII collagen found in circulation related with disease activity of DSS rats.

To further validate the PRO-C23 biomarker, it was measured in two human cohorts. PRO-C23 was elevated in human CD patients (cohort 2) and in UC patients (cohort 3) with active disease. These data suggested the release of ectodomain of type XXIII collagen was reinforced in the active intestinal damage, which was consistent with the results in animal model.

Type XXIII collagen has been suggested to be a potential biomarker for prostate cancer recurrence [18], non-small cell lung cancer [17] and clear cell renal cell carcinoma [14]. It showed significantly higher expression in those cancer tissues, especially in the metastatic tissue. It is believed that type XXIII collagen facilitates cell-cell adhesion and cell-matrix adhesion [13]. Silencing type XXIII collagen in lung cancer and clear cell renal cell lines showed altered adhesion protein expressions and less ability on cell adhesion and migration [13,14]. However, type XXIII collagen is also present in other tissue, and the function and the use in other diseases are yet unknown. To the inventors' knowledge, this is the first study that showed type XXIII collagen level was modulated in IBD. The results indicate that type XXIII collagen may also play an important role in cell adhesion in intestines and contribute to the pathologies of IBD.

CONCLUSION

The data indicates that the biomarkers of epithelium PRO-C23 can be used as non-invasive surrogates of disease activity in CD patients and thus aid in monitoring patients. Higher levels of PRO-C23 were measured in serum of CD and UC patients with active disease compared to inactive disease.

All prior teachings acknowledged in this specification are hereby incorporated by reference. No acknowledgement of any prior published document herein should be taken to be an admission or representation that the teaching thereof was common general knowledge in Australia or elsewhere at the date hereof.

REFERENCES

[1] K. J. Maloy, F. Powrie, Intestinal homeostasis and its breakdown in inflammatory bowel disease, Nature. 474 (2011) 298-306. doi:10.1038/nature10208.

[2] D. C. Baumgart, W. J. Sandborn, Crohn's disease, Lancet. 380 (2012) 1590-1605. doi:10.1016/S0140-6736 (12)60026-9.

[3] P. Brandtzaeg, The gut as communicator between environment and host: Immunological consequences, in: Eur. J. Pharmacol., 2011. doi:10.1016/j.ejphar.2011.07.006.

[4] S. Broer, Amino Acid Transport Across Mammalian Intestinal and Renal Epithelia, Physiol. Rev. 88 (2008) 249-286. doi:10.1152/physrev.00018.2006.

[5] S. C. Bischoff, G. Barbara, W. Buurman, T. Ockhuizen, J. D. Schulzke, M. Serino, H. Tilg, A. Watson, J. M. Wells, Intestinal permeability—a new target for disease prevention and therapy, BMC Gastroenterol. 14 (2014). doi: 10.1186/s12876-014-0189-7.

[6] K. R. Groschwitz, S. P. Hogan, Intestinal barrier function: molecular regulation and disease pathogenesis, J. Allergy Clin. Immunol. 124 (2009) 3-20-2. doi:10.1016/ j.jaci. 2009.05.038.

[7] J. Chang, R. W. Leong, V. C. Wasinger, M. Ip, M. Yang, T. G. Phan, Impaired Intestinal Permeability Contributes to Ongoing Bowel Symptoms in Patients With Inflammatory Bowel Disease and Mucosal Healing, Gastroenterology. 153 (2017) 723-731.e1. doi:10.1053/j.gastro.2017.05.056.

[8] N. Gassler, C. Rohr, a Schneider, J. Kartenbeck, a Bach, N. Obermüller, H. F. Otto, F. Autschbach, Inflammatory bowel disease is associated with changes of enterocytic junctions, Am. J. Physiol. Gastrointest. Liver Physiol. 281 (2001) G216-G228. doi:10.1152/ajpgi.2001.281.1.G216.

[9] H. Ohta, Y. Sunden, N. Yokoyama, T. Osuga, S. Y. Lim, Y. Tamura, K. Morishita, K. Nakamura, M. Yamasaki, M. Takiguchi, Expression of apical junction complex proteins in duodenal mucosa of dogs with inflammatory bowel disease, Am. J. Vet. Res. 75 (2014) 746-751. doi:10.2460/ajvr.75.8.746.

[10] A. J. Karayiannakis, K. N. Syrigos, J. Efstathiou, A. Valizadeh, M. Noda, R. J. Playford, W. Kmiot, M. Pignatelli, Expression of catenins and E-cadherin during epithelial restitution in inflammatory bowel disease, J. Pathol. 185 (1998) 413-418. doi:10.1002/(SICI)1096-9896(199808)185:4<413:: AID-PATH125>3.0.00; 2-K.

[11] A. Dogan, Z. D. Wang, J. Spencer, E-cadherin expression in intestinal epithelium, J Clin Pathol. 48 (1995) 143-146. doi:10.1136/jcp.48.2.143.

[12] J. Banyard, L. Bao, B. R. Zetter, Type XXIII collagen, a new transmembrane collagen identified in metastatic tumor cells, J. Biol. Chem. 278 (2003) 20989-20994. doi:10.1074/jbc.M210616200.

[13] K. A. Spivey, I. Chung, J. Banyard, I. Adini, H. A. Feldman, B. R. Zetter, A role for collagen XXIII in cancer cell adhesion, anchorage-independence and metastasis, Oncogene. 31 (2012) 2362-2372. doi:10.1038/ onc.2011.406.

[14] F. Xu, K. Chang, J. Ma, Y. Qu, H. Xie, B. Dai, H. Gan, H. Zhang, G. Shi, Y. Zhu, Y. Zhu, Y. Shen, D. Ye, The Oncogenic Role of COL23A1 in Clear Cell Renal Cell Carcinoma, Sci. Rep. 7 (2017) 9846. doi:10.1038/s41598-017-10134-2.

[15] M. Koch, G. Veit, S. Stricker, P. Bhatt, S. Kutsch, P. Zhou, E. Reinders, R. A. Hahn, R. Song, R. E. Burgeson, D. R. Gerecke, S. Mundlos, M. K. Gordon, Expression of type XXIII collagen mRNA and protein, J. Biol. Chem. 281 (2006) 21546-21557. doi:10.1074/jbc.M604131200.

[16] G. Veit, E. P. Zimina, C. W. Franzke, S. Kutsch, U. Siebolds, M. K. Gordon, L. Bruckner-Tuderman, M. Koch, Shedding of collagen XXIII is mediated by furin and depends on the plasma membrane microenvironment, J. Biol. Chem. 282 (2007) 27424-27435. doi:10.1074/ jbc.M703425200.

[17] K. A. Spivey, J. Banyard, L. M. Solis, Wistuba II, J. A. Barletta, L. Gandhi, H. A. Feldman, S. J. Rodig, L. R. Chirieac, B. R. Zetter, Collagen XXIII: a potential biomarker for the detection of primary and recurrent non-small cell lung cancer, Cancer Epidemiol Biomarkers Prev. 19 (2010) 1362-1372. doi:10.1158/1055-9965.EPI-09-1095.

[18] J. Banyard, L. Bao, M. D. Hofer, D. Zurakowski, K. A. Spivey, A. S. Feldman, L. M. Hutchinson, R. Kuefer, M. A. Rubin, B. R. Zetter, Collagen XXIII Expression Is Associated with Prostate Cancer Recurrence and Distant Metastases, Clin. Cancer Res. 13 (2007) 2634-2642. doi:10.1158/1078-0432.CCR-06-2163.

[19] M. B. Wozniak, F. Le Calvez-Kelm, B. Abedi-Ardekani, G. Byrnes, G. Durand, C. Carreira, J. Michelon, V. Janout, I. Holcatova, L. Foretova, A. Brisuda, F. Lesueur, J. McKay, P. Brennan, G. Scelo, Integrative Genome-Wide Gene Expression Profiling of Clear Cell Renal Cell Carcinoma in Czech Republic and in the United States, PLoS One. 8 (2013). doi:10.1371/journal.pone.0057886.

[20] R. D'Incà, V. Di Leo, G. Corrao, D. Martines, A. D'Odorico, C. Mestriner, C. Venturi, G. Longo, G. C. Sturniolo, Intestinal permeability test as a predictor of clinical course in Crohn's disease, Am. J. Gastroenterol. 94 (1999) 2956-60. doi:10.1111/j.1572-0241.1999.01444.x.

[21] G. D'Haens, M. Ferrante, S. Vermeire, F. Baert, M. Noman, L. Moortgat, P. Geens, D. Iwens, I. Aerden, G. Van Assche, G. Van Olmen, P. Rutgeerts, Fecal calprotectin is a surrogate marker for endoscopic lesions in inflammatory bowel disease, Inflamm. Bowel Dis. 18 (2012) 2218-2224. doi:10.1002/ibd.22917.

[22] R. Mao, Y. L. Xiao, X. Gao, B. L. Chen, Y. He, L. Yang, P. J. Hu, M. H. Chen, Fecal calprotectin in predicting relapse of inflammatory bowel diseases: A meta-analysis of prospective studies, Inflamm. Bowel Dis. 18 (2012) 1894-1899. doi:10.1002/ibd.22861.

[23] T. Sipponen, E. Savilahti, P. Kärkkäinen, K. L. Kolho, H. Nuutinen, U. Turunen, M. Färkkilä, Fecal calprotectin, lactoferrin, and endoscopic disease activity in monitoring anti-TNF-alpha therapy for Crohn's disease, Inflamm. Bowel Dis. 14 (2008) 1392-1398. doi:10.1002/ibd.20490.

[24] G. Thuijls, J. P. M. Derikx, J. J. de Haan, J. Grootjans, A. de Bruïne, A. A. M. Masclee, E. Heineman, W. A. Buurman, Urine-based Detection of Intestinal Tight Junction Loss, J. Clin. Gastroenterol. 44 (2010) e14-e19. doi:10.1097/MCG.0b013e31819f5652.

[25] P. Kiesler, I. J. Fuss, W. Strober, Experimental Models of Inflammatory Bowel Diseases, C. Cell. Mol. Gastroenterol. Hepatol. 1 (2015) 154-170. doi:10.1016/j.jcmgh.2015.01.006.

[26] J. J. Kim, M. S. Shajib, M. M. Manocha, W. I. Khan, Investigating Intestinal Inflammation in DSS-induced Model of IBD, J. Vis. Exp. (2012). doi:10.3791/3678.

[27] L. S. Poritz, K. I. Garver, C. Green, L. Fitzpatrick, F. Ruggiero, W. A. Koltun, Loss of the Tight Junction Protein ZO-1 in Dextran Sulfate Sodium Induced Colitis, J. Surg. Res. 140 (2007) 12-19. doi:10.1016/j.jss.2006.07.050.

[28] Kabat, E. A., T. T. Wu, H. M. Perry, K. S. Gottesman and C. Foeller (1987), Sequences of Proteins of Immunological Interest, United States Department of Health and Human Services, Bethesda, Md., p. 1

The invention claimed is:

1. A monoclonal antibody that specifically recognises and binds to a peptide having the C-terminus amino acid sequence GLPVPGCWHK (SEQ. ID NO: 1); wherein the monoclonal antibody or fragment thereof comprises complementarity-determining regions (CDRs):

```
CDR-H1:
                            (SEQ. ID NO: 6)
SYAMS,

CDR-H2:
                            (SEQ. ID NO: 7)
SISTAGRTYYPDTVR,

CDR-H3:
                            (SEQ. ID NO: 8)
PDYDYDGYIN,

CDR-L1:
                            (SEQ. ID NO: 9)
RSSKSLLHSNGVTYLY,

CDR-L2:
                            (SEQ. ID NO: 10)
QMSNLAS,
and

CDR-L3:
                            (SEQ. ID NO: 11)
AQNLELPLT.
```

2. A method of immunoassay for detecting type XXIII collagen in a human biofluid sample, said method comprising contacting a human biofluid sample with a monoclonal antibody that specifically recognises and binds to a peptide having the C-terminus amino acid sequence GLPVPGCWHK (SEQ. ID NO: 1), and detecting binding between the monoclonal antibody and peptides in the sample; wherein the monoclonal antibody or fragment thereof comprises complementarity-determining regions (CDRs):

```
CDR-H1:
                            (SEQ. ID NO: 6)
SYAMS,

CDR-H2:
                            (SEQ. ID NO: 7)
SISTAGRTYYPDTVR,

CDR-H3:
                            (SEQ. ID NO: 8)
PDYDYDGYIN,

CDR-L1:
                            (SEQ. ID NO: 9)
RSSKSLLHSNGVTYLY,

CDR-L2:
                            (SEQ. ID NO: 10)
QMSNLAS, and

CDR-L3:
                            (SEQ. ID NO: 11)
AQNLELPLT.
```

3. The method of claim 2, wherein the detection is quantitative.

4. The method of claim 2, wherein the immunoassay is a competitive immunoassay.

5. The method of claim 2, wherein the monoclonal antibody is a monoclonal antibody raised against a synthetic peptide having the C-terminus amino acid sequence GLPVPGCWHK (SEQ. ID NO: 1).

6. The method of claim 2, wherein the human biofluid sample is from a human patient having medical signs or symptoms indicative of inflammatory bowel disease.

7. The method of claim 6 wherein the inflammatory bowel disease is Crohn's disease or ulcerative colitis.

8. The method of claim 2, wherein the method is an immunoassay method for diagnosing and/or monitoring and/or assessing the likelihood of inflammatory bowel disease in a patient, the method comprising contacting a biofluid sample obtained from said patient with the monoclonal antibody, detecting and determining the amount of binding between the monoclonal antibody and peptides in the sample, and correlating said amount of binding with values associated with normal healthy subjects and/or values associated with known disease severity and/or values obtained from said patient at a previous time point.

9. An assay kit comprising a monoclonal antibody that specifically recognises and binds to a peptide having the C-terminus amino acid sequence GLPVPGCWHK (SEQ. ID NO: 1), and at least one of:
 a streptavidin coated well plate;
 a N-terminal biotinylated peptide having the C-terminus amino acid sequence GLPVPGCWHK (SEQ. ID NO: 1); and
 a calibrator peptide having the C-terminus amino acid sequence GLPVPGCWHK (SEQ. ID NO: 1); wherein the monoclonal antibody or fragment thereof comprises complementarity-determining regions (CDRs):

```
CDR-H1:
                            (SEQ. ID NO: 6)
SYAMS,

CDR-H2:
                            (SEQ. ID NO: 7)
SISTAGRTYYPDTVR,

CDR-H3:
                            (SEQ. ID NO: 8)
PDYDYDGYIN,

CDR-L1:
                            (SEQ. ID NO: 9)
RSSKSLLHSNGVTYLY,

CDR-L2:
                            (SEQ. ID NO: 10)
QMSNLAS, and

CDR-L3:
                            (SEQ. ID NO: 11)
AQNLELPLT.
```

10. The assay kit of claim 9, wherein the monoclonal antibody is a monoclonal antibody raised against a synthetic peptide having the C-terminus amino acid sequence GLPVPGCWHK (SEQ. ID NO: 1).

* * * * *